(12) United States Patent
Deshpande et al.

(10) Patent No.: US 7,446,200 B2
(45) Date of Patent: Nov. 4, 2008

(54) RAPID RESOLUTION PROCESS OF CLOPIDOGREL BASE AND A PROCESS FOR PREPARATION OF CLOPIDOGREL BISULFATE POLYMORPH-FORM I

(75) Inventors: Manoj Madhukarrao Deshpande, Mumbai (IN); V. R. Tarur, Mumbai (IN); Dhananjay Govind Sathe, Thane (IN); Harish Kashniath Mondkar, Mumbai (IN); Kamlesh Digambar Sawant, Mumbai (IN); Tushar Anil Naik, Mumbai (IN)

(73) Assignee: USV, Ltd., Mumbai (IN)

( * ) Notice: Subject to any disclaimer, the term of this patent is extended or adjusted under 35 U.S.C. 154(b) by 345 days.

(21) Appl. No.: 11/149,646

(22) Filed: Jun. 10, 2005

(65) Prior Publication Data

US 2006/0074242 A1  Apr. 6, 2006

Related U.S. Application Data

(63) Continuation-in-part of application No. 10/957,891, filed on Oct. 4, 2004, now abandoned.

(30) Foreign Application Priority Data

Feb. 15, 2005 (IN) .................. PCT/IN05/00048

(51) Int. Cl.
*C07D 495/04* (2006.01)
(52) U.S. Cl. ..................................... 546/114
(58) Field of Classification Search .................. 546/114
See application file for complete search history.

(56) References Cited

U.S. PATENT DOCUMENTS

| 4,847,265 A | 7/1989 | Badorc et al. |
| 6,429,210 B1 | 8/2002 | Bousquet et al. |
| 6,737,411 B2 | 5/2004 | Valeriano et al. |
| 6,800,759 B2 | 10/2004 | Valeriano et al. |

FOREIGN PATENT DOCUMENTS

| WO | WO04/74215 | 9/2004 |
| WO | 104663 | * 11/2005 |

* cited by examiner

*Primary Examiner*—Patricia L. Morris
(74) *Attorney, Agent, or Firm*—Pharmaceutical Patent Atty's, LLC

(57) ABSTRACT

The present invention discloses a rapid resolution process of racemic clopidogrel base followed by conversion of the resolved (S) isomer to crystalline Clopidogrel bisulfate Form I. The invention also discloses novel racemization process of the unwanted (R) isomer of clopidogrel base. The invention further discloses an improved process for preparation of acid addition salts of clopidogrel.

15 Claims, 3 Drawing Sheets

RAPID RESOLUTION PROCESS OF CLOPIDOGREL BASE AND A PROCESS FOR PREPARATION OF CLOPIDOGREL BISULFATE POLYMORPH-FORM I

RELATED APPLICATIONS

This application is a continuation in part of co-pending U.S. Ser. No. 10/957,891, incorporated herein by reference. This application claims priority from Patent Cooperation Treaty Application Serial No. PCT/IN05/00048, filed 15 Feb. 2005, the contents of which are incorporated herein by reference.

TECHNICAL FIELD

The present invention relates to a rapid resolution process of racemic clopidogrel base followed by conversion of the resolved (S) isomer to crystalline Clopidogrel bisulfate Form I. Clopidogrel bisulfate [Formula I] [Methyl (S)–(+)–α(o-chlorophenyl)- 6,7-dihydrothieno [3,2- c] pyridine- 5 (4H)-acetate hydrogen sulfate] is an Antithrombotic agent.

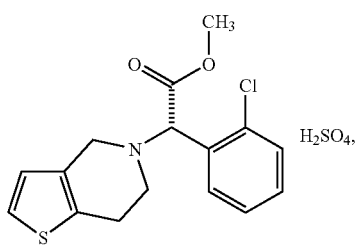

Formula I

BACKGROUND

Clopidogrel is administrated as its hydrogensulfate (syn. Bisulfate) salt. Its antiplatelet activity makes it an effective drug for reducing ischemic strokes, heart attacks and in atherosclerosis (a vascular disease causing claudication). Atherosclerosis is a buildup of plaque in the walls of arteries, which leads to thickening, and the reduction in the elasticity of the arteries. High Cholesterol, high blood pressure, smoking and infection also causes an injury to the inner walls of the arteries, which leads to the atherosclerosis. The plaque formation leads to blood clotting which is due to the platelet aggregation at the site of the injury. This clotting becomes an obstacle for the flow of the blood to the vital organs causing heart attacks or other severe problems.

Antiplatelet activity which fights against Atherosclerosis is exhibited by Clopidogrel, which binds adenosine diphosphate to its receptor and thereby induces platelet reduction, which is desirable in fighting against atherosclerosis. Clopidogrel has found to be more effective in inhibiting platelet aggregation than aspirin and is also mild towards gastrointestinal tract. (S) enantiomer of clopidogrel is pharmaceutically active and is administrated as bisulfate salt.

U.S. Pat. No. 4,529,596, discloses a racemic mixture of clopidogrel bisulfate and process for preparation of such mixture, which involves condensation reaction between methyl-2-chloro-o-chlorophenylacetate and 4,5,6,7-tetrahydro thieno[3,2-c]pyridine. The reaction produces racemic clopidogrel.

U.S. Pat. No. 4,847,265 discloses process for preparation of the dextro-rotatory enantiomer of the clopidogrel bisulfate. Racemic clopidogrel is resolved using camphor sulfonic acid to obtain optically pure dextro rotatory isomer. The patent describes the crystallization of the (S) enantiomer using dimethylformamide, ketones and alcohols. Amongst ketones, acetone is used for crystallization.

U.S.Pat. No. 5,036,156, discloses a method for preparation of an intermediate in the synthesis of clopidogrel, 2-chloro-αbromophenyl acetic acid and a process for condensing methyl ester with tetrahydrothienopyridine. The patent also describes process for preparation of pyridine derivative, which is one of the intermediate for preparation of clopidogrel.

U.S. Pat. No. 6,080,875 describes a process for preparation of methyl (+)-(S)-a-(2-thienyl-2-ethylamino)-a-(2-chlorophenyl)acetate hydrochloride by reaction of sodium-2-thienylglycidate with (S) 2-chloro phenyl glycine in presence of cyanoborohydride. This intermediate is further used to prepare (S) clopidogrel. The patent also describes the process for recemization of phenyl glycine esters.

U.S. Pat. No. 6,180,793 describes a process for preparation of (S) clopidogrel by reaction of 2-thiophene ethanol with (S)-2- chlorophenyl glycineamide, (S)-2-chlorophenyl-α-amino acetonirile or (S)-2-chlorophenyl glycine methyl ester. The resulting compound is cyclised, hydrolysed and esterified.

U.S. Pat. No. 5,204,469 discloses enantioselective process for preparation of clopidogrel through the reaction of (+)-2-chlorophenyl glycine and an activated form of 2-thiophene ethanol followed by cyclization with formaldehyde.

U.S. Pat. No. 6,800,759 describes a process for resolution of racemic clopidogrel, along with the conversion of (R) enantiomer of the clopidogrel to (S). The (S) enatiomer is separated by crystallizing it as camphor sulfonate salt from hydrocarbon, or a mixture of hydrocarbon and a co-solvent, preferably DMF:Toluene. The (R) enantiomer is then racemized and recycled by reaction with catalytic amount of base. The bases used are metal alkoxide, preferably potassium-t-butoxide.

U.S. Pat. No. 4,847,265 describes the formation of the dextrorotatory isomer of clopidogrel by salt formation using racemic compound and an optically active acid such as 10-L-camphorsulfonic acid in acetone, followed by successive recrystallisation until a product with constant rotatory power was obtained, followed by the release of the dextro rotatory isomer from its salt by a base. The hydrogen sulfate salt is then obtained by dissolution of the base in acetone cooled in ice and addition of concentrated sulphuric acid to precipitation. The precipitate thus obtained is crystalline Form I.

WO 98/39286 discloses racemization process for phenyl glycine ester in which a mixture of enantiomer of phenyl glycine ester is treated with a carbonyl compound in presence of carboxylic acid and single enantiomer of an N-protected-a-amino acid as a resolving agent. The formation of the imino intermediate causes the racemisation of the starting product and the precipitation of the single diastereomeric salt. After hydrolysis of the salt, an enantiomer of phenyl glycine ester is obtained.

WO/04/074215 discloses racemization process of (R) clopidogrel which involve conversion of (R) isomer to its racemic salt such as Hydrochloride, which is formed by dissolution of (R) Clopidogrel in Isopropyl alcohol and concentrated HCl. The salt thus formed is further converted to Racemic Clopidogrel base by treatment with base.

WO2004013147 describes a process for racemization of (R) isomer of the clopidogrel by the reaction with catalytic amount of the base preferably with potassium t-butoxide.

U.S. Pat. No. 6,429,210 describe process for preparation of the dextrorotatory S enantiomer of Clopidogrel bisulfate in the crystalline Form, Form II.

US2003114479 describes the novel crystalline forms, Form III, IV and V of clopidogrel hydrogen sulphate and amorphous form of clopidogrel hydrogen sulphate and processes for preparation of these forms and amorphous form as well as their pharmaceutical compositions. In this patent, polymorphic Form I is prepared by suspending amorphous clopidogrel hydrogen sulphate in ether.

International Patent application WO2004020443 describes process for preparation of Clopidogrel bisulfate Form I, which comprises separating out crystalline Form I from the solution of clopidogrel in the form of free base or salt in a solvent selected from the series of the primary, secondary or tertiary C1-C5 alcohols or their Esters with C1-C4 carboxylic acids or optionally of mixtures thereof.

International application WO 2004048385 describes a process for the preparation of crystalline Form I of S-Clopidogrel hydrogen sulphate by reacting the optically active base, (S)-(+) clopidogrel with concentrated sulfuric acid, wherein the salt formed by the said reaction in the reaction medium is precipitated with the precipitating solvent such as aliphatic or cyclic ethers and/or their mixture or isobutyl methyl ketone.

Form II of Clopidogrel Bisulfate is thermodynamically more stable and hence small change in condition during the preparation of Form I can result in Form II.

The present invention relates to the novel process for resolution of racemic clopidogrel base followed by conversion of the resolved (S) isomer to crystalline Clopidogrel bisulfate Form I. The present invention also relates to the racemization of unwanted (R) isomer. The present invention also relates to a process for resolution of clopidogrel base which is simple and less time consuming. The present invention also relates to the process for preparation of crystalline Form I of Clopidogrel Bisulfate from (S) clopidogrel base, which is reproducible. The present invention also relates to the process for preparation of crystalline Form I of Clopidogrel Bisulfate, which is cost effective and economical. The present invention also relates to the process for preparation of crystalline Form I of Clopidogrel Bisulfate, which is commercially viable.

SUMMARY

The present invention discloses novel process for resolution of racemic clopidogrel base followed by conversion of the resolved (S) isomer to crystalline Clopidogrel bisulfate Form I. The present invention also discloses the racemization of unwanted (R) isomer and further resolution to pure (S) isomer. The present invention further discloses the preparation of crystalline Form of Clopidogrel Bisulfate Form I, by dissolving (S) Clopidogrel base in a solvent such as acetic acid and adding antisolvent such as di-isopropyl ether containing sulfuric acid.

In order to lower the time period and initiate the fast crystallization of the (S) clopidogrel camphorsulfonate salt, the resolution is carried out in a mixture of solvent which comprises aliphatic ketones preferably Acetone and acyclic simple ethers like Diisopropyl ether, methyl-tert-butyl ether, diethyl ether, preferably methyl-tert-butyl ether (MTBE). The resolution takes place within 4 Hrs to 10 Hrs.

The unwanted (R) isomer separated during the resolution is further converted to (S) isomer by dissolving the (R)-isomer in $C_5$-$C_7$ aliphatic hydrocarbon/$C_1$-$C_5$ alcohols/or aliphatic ethers like di ethyl ether, methyl-t-butyl ether, di isopropyl ether, Tetrahydrofuran (THF), 1,4-Dioxane, as solvents containing base such as metal alkoxide. The resolved (S) Clopidogrel base is dissolved in a solvent such as acetic acid and adding antisolvent such as di-isopropyl ether containing sulfuric acid to get the crystalline Form I of Clopidogrel bisulfate.

DETAILED DESCRIPTION

The present invention relates to the novel process for resolution of racemic clopidogrel base followed by conversion of the resolved (S) isomer to crystalline Clopidogrel bisulfate Form I. The present invention also relates to the racemization of unwanted (R) isomer of Clopidogrel base. The process is shown as below,

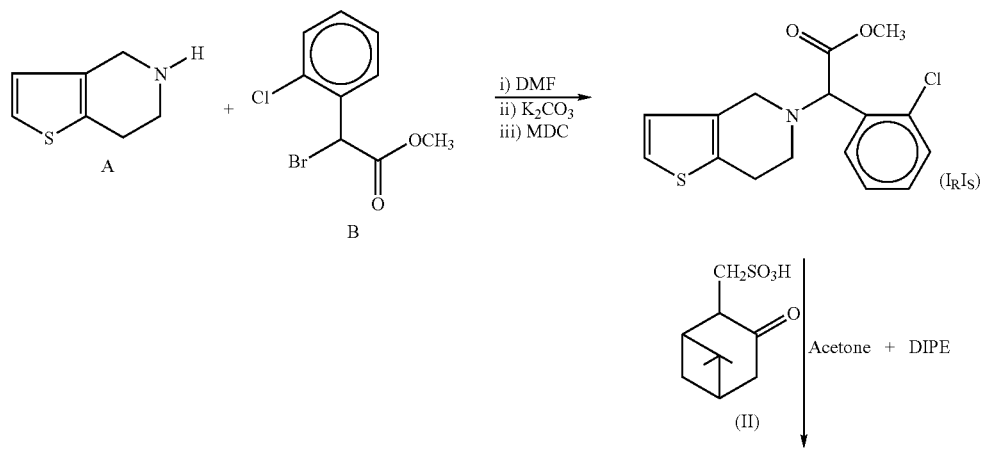

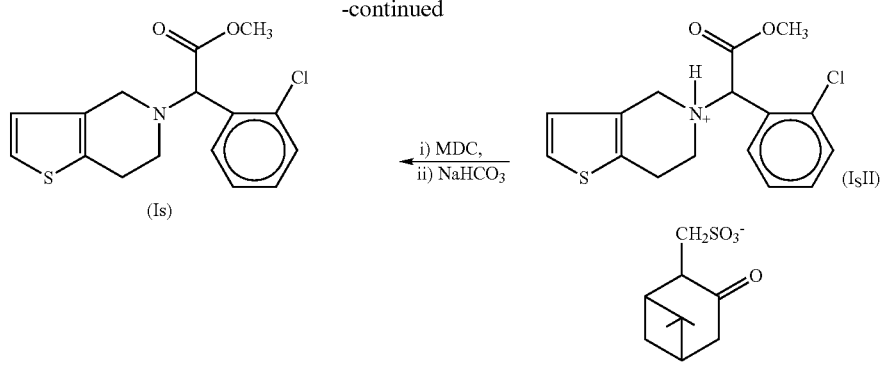

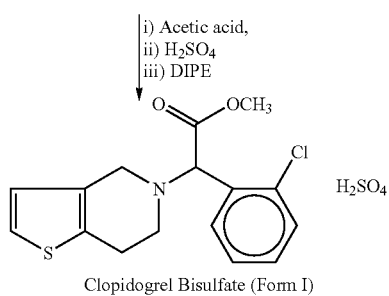

Clopidogrel Bisulfate (Form I)

The manufacturing process described in this invention involves preparation of racemic Clopidogrel by the process similar to described in U.S. Pat. No. 4,529,596. The said process comprises, condensation of the 4,5,6,7-tetrahydrothieno[3,2-c]pyridine hydrochloride (A) and α-bromo-2-chlorophenyl acetic acid methyl ester (B) in DMF in presence of potassium carbonate, which gives racemic clopidogrel free base ($I_R I_S$). The process is shown below.

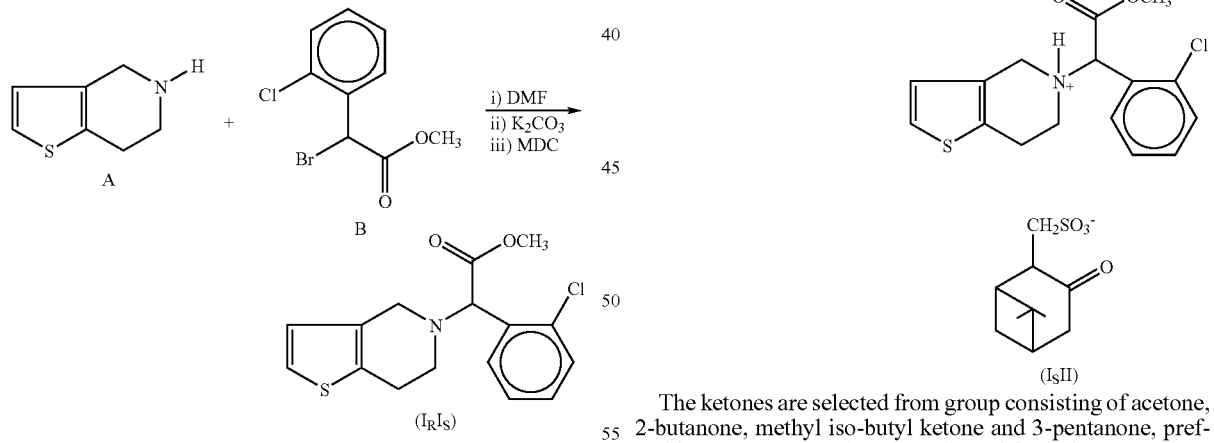

The present invention relates to rapid and simple process for resolution of (S) clopidogrel base ($I_S$) which, comprises the steps of reacting a mixture of (R) and (S) clopidogrel base ($I_R I_S$) with laevo rotatory camphor sulfonic acid (II) in a mixture of solvents to precipitate (S) clopidogrel camphor sulfonate.

The Chiral, laevo rotatory camphor-10-sulfonic acid of formula (II) is allowed to react with the racemic clopidogrel base of Formula ($I_R I_S$) in the mixture of solvent comprises a ketone and/or an aliphatic ether according to following scheme.

The ketones are selected from group consisting of acetone, 2-butanone, methyl iso-butyl ketone and 3-pentanone, preferably acetone. The ethers are selected from the group comprising of di ethyl ether, methyl-t-butyl ether, di isopropyl ether, THF and 1,4-Dioxane, preferably methyl-tert-butyl ether. The mixture of solvent is about 10% v/v to about 50% v/v of ether in acetone preferably 50% v/v.

The (S) Clopidogrel camphor sulfonate salt ($I_S II$) is further purified with ketonic solvents like acetone, 2-butanone, 3-pentanone, methyl-tert-butyl ketone.

Converting the (S) Clopidogrel camphor sulfonate salt ($I_S II$) to (S) Clopidogrel free base of formula ($I_S$) by the conventional technique. Dissolving the resolved (S) Clopidogrel base ($I_S$) in glacial acetic acid at room temperature; followed by adding an antisolvent containing sulfuric acid to the solution at room temperature. Stirring the reaction mixture for 24 hours at room temperature, filtering and drying the crystals to obtain Form I of Clopidogrel Bisulfate.

The unwanted (R) isomer Clopidogrel base ($I_R$) enriched in the mother liquor of resolution is diluted with ether, washed with sodium bicarbonate solution to remove camphor sulfonate. The ether layer containing the enriched unwanted (R) Clopidogrel base ($I_R$) isomer is treated with a base such as metal alkoxide preferably potassium-t-butoxide to get back racemic clopidogrel base ($I_R I_S$) which is then resolved again as earlier described. This process is shown in the following scheme.

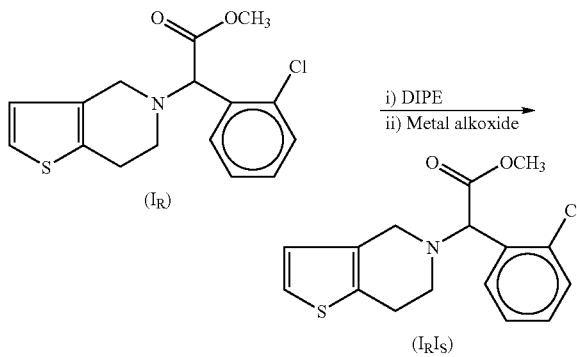

The entire sequence of the process is shown below,

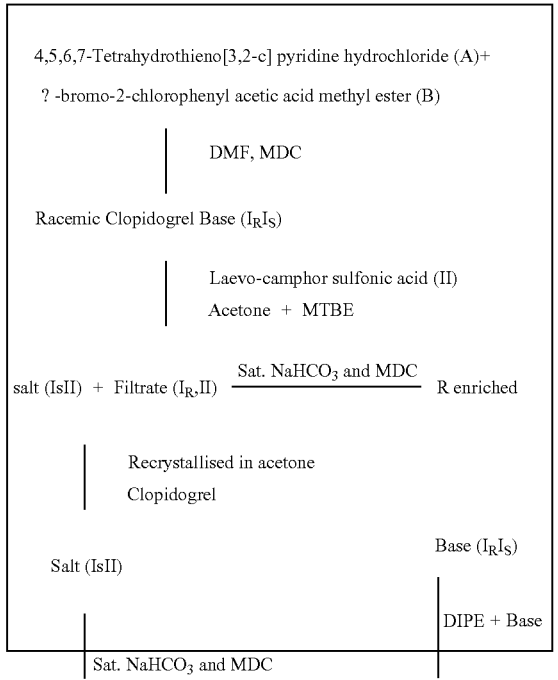

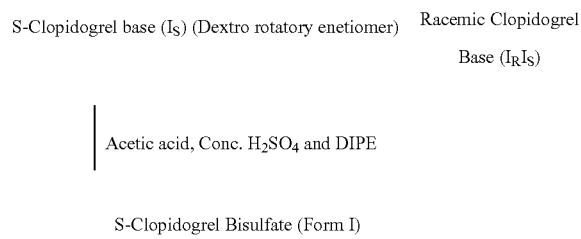

As used herein, a solvent is any liquid substance, which has capacity to dissolve the organic compound, Clopidogrel Bisulfate, either at room temperature or higher temperature. Antisolvent is an organic solvent in which organic compound such as Clopidogrel Bisulfate has poor solubility.

As used herein, room temperature means a temperature from about 10° C. to 45° C., preferably 25° C. to 30° C.

The quality of clopidogrel bisulfate of Form I without detectable contamination by Form II, obtained in accordance with this invention, is characterized by X-Ray crystallographic data, Differential Scanning Calorimeter and Fourier-transform infrared (FT-IR) spectrum.

X-ray powder diffraction pattern has been obtained on D 8-Advance, Bruker AXE, Germany, diffractometer equipped with Scintillation detector using Copper $K\alpha(\lambda=0.5406$ Å) radiation with scanning range between 2-50 at scanning speed of 2°/min.

Differential Scanning Calorimeter was performed on Mettler DSC 20 instrument. Samples of 2 mg to 3 mg weighed in aluminium crucibles with holes were scanned at a heating rate of 10° C. per minute under nitrogen atmosphere at rate of 35 ml/min.

The Fourier-transform infrared (FT-IR) spectrum of Form I was obtained on a FT-IR 8300, Shimadzu instrument, in the range of 400-4000 $cm^{-1}$ with a resolution of 4 $m^{-1}$. The spectrum is entirely different from the spectrum of Form II disclosed in patent U.S. Pat. No. 6,429,210.

BRIEF DESCRIPTION OF THE FIGURES

FIG. 1 of the polymorphic form obtained by this method, Form I shows an X-ray powder diffraction pattern which is characterized by having peaks at about 9.21, 9.56, 14.85, 15.53, 15.23, 20.62, 21.59, 23.19, 23.85, 25.52, ±0.2 degrees. FIG. 2 shows the DSC thermogram of Form I which is characterized by having sharp endotherm at 187° C. followed by another sharp endotherm at 212° C. The FT-IR spectrum of Form I shows absorption at 2987, 2952, 1751, 1477, 1436, 1220, 1191, 867, 841, 766, 592 $cm^{-1}$ which is shown in FIG. 3.

Figure 1:
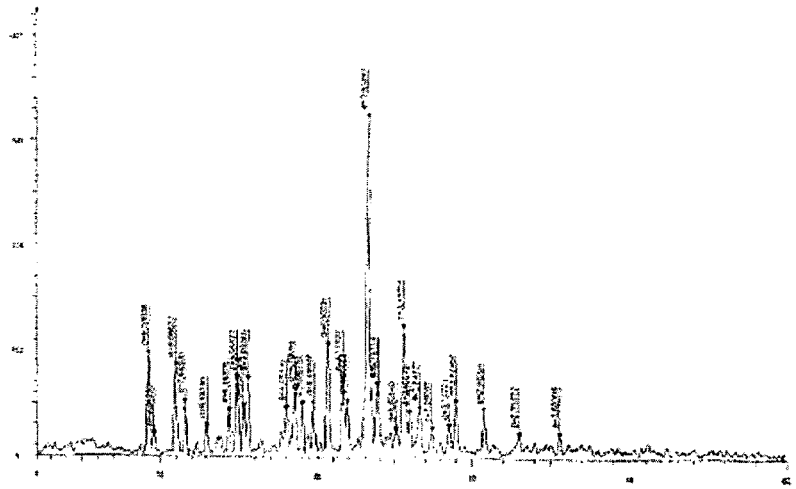
FIG. 1 Shows the X-ray Diffraction Diagram of Clopidogrel Bisulfate Form I
Figure 2:
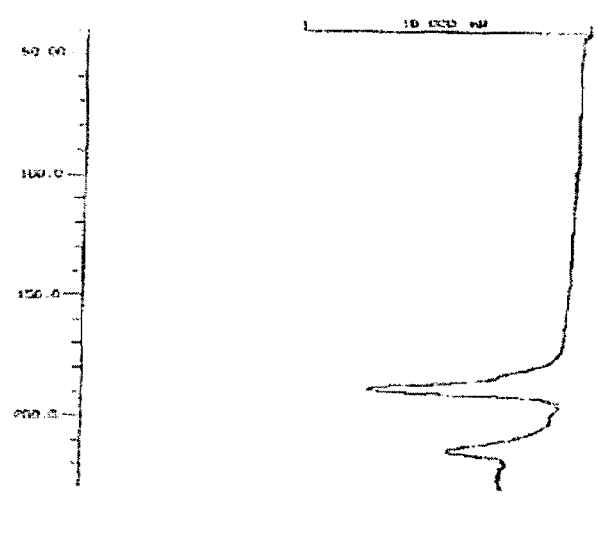
FIG. 2 Shows the DSC Thermogram of Clopidogrel Bisulfate Form I
Figure 3:
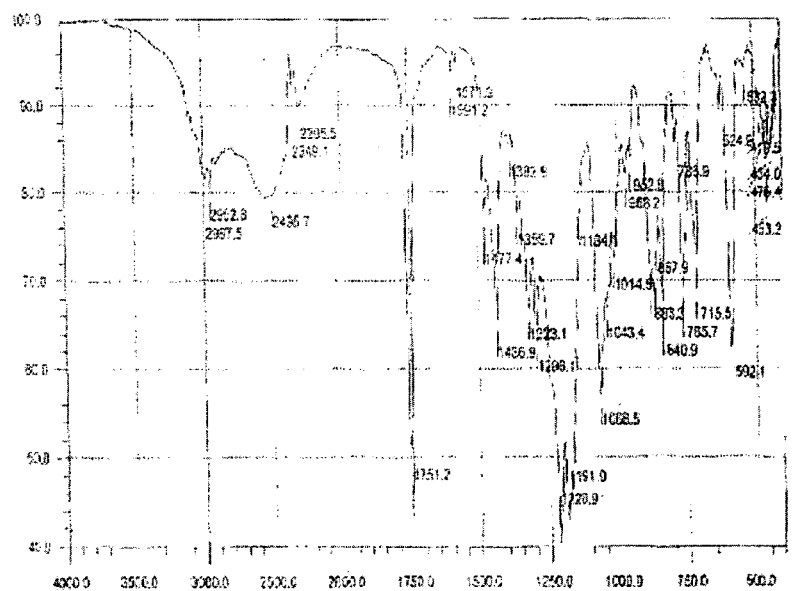
FIG. 3 Shows the FT-IR Spectrum of Clopidogrel Bisulfate Form I

The following examples are provided to illustrate the invention and are not limiting the scope of the complete disclosure.

EXAMPLE 1

Synthesis of Racemic Clopidogrel Base ($I_R I_S$)

50 g (0.284 mole) of Tetrahydrothienopyridine hydrochloride (A) was reacted with 83 g (0.315 mole) of α-bromo-2-chlorophenyl acetic acid methyl ester (B) in 2.5 Lt. DMF in presence of 83 g. (0.6 mole) potassium carbonate. The reaction mixture was heated at 80-85°C under nitrogen atmosphere for 4 Hrs. The reaction mixture was filtered at RT and washed the residue with DMF. The DMF was concentrated under vacuum to obtain a viscous liquid. To this viscous liquid, water was added and the base was extracted from the aqueous layer using methylene dichloride. The methylene dichloride was concentrated under vacuum to get pure Clopidogrel base. Yield =92%

EXAMPLE 2

Resolution of Racemic Clopidogrel Base ($I_RI_S$)

a) Conversion of Racemic Clopidogrel Base ($I_RI_S$) to (S) Clopidogrel Camphor Sulfonate Salt ($I_SII$).

10 g (0.03 mole) of Racemic clopidogrel obtained from Example 1 was dissolved in 20 ml Methyl-tert-butyl-ether and to this 3.82 (0.016 mole) g. of L-(-)-Camphor sulfonic acid was added. To this solution 20 ml acetone was added to get the clear solution. The solution was stirred at 50° C. for 8 Hrs. Filter the solid separated and washed with acetone and dried under vacuum at 50° C. m.p 163-165, $[?]_D^{20}$=24.7, yield=58% b) Conversion of (S) Clopidogrel Camphor Sulfonate Salt ($I_SII$) to (S) Clopidogrel Base ($I_S$).

5 g (0.009 mole) of the (S) Clopidogrel camphor sulfonate salt obtained from example 2 was suspended in 20 ml MDC. To this add 20 ml aqueous solution of saturated sodium bicarbonate. After vigorous stirring, the organic phase was separated and dried over sodium sulfate. The solvent was removed under reduced pressure. The residue obtained was (S) Clopidogrel Base. Yield=97%

EXAMPLE 3

Preparation of Clopidogrel Bisulfate Form I From (S) Clopidogrel Base ($I_S$)

5 g (0.015 mole) of (S) Clopidogrel was dissolved in 25 ml of Glacial acetic acid at room temperature. The solution was filtered to remove any suspended particles. This clear solution was added to 200 ml of Di isopropyl ether containing 1.5 g (0.015 mole) conc. $H_2SO_4$ was added drop wise at the 10° C. The solution was stirred for 6 hrs. at the same temperature and further 10 Hrs at room temperaturte. The solid was filtered, washed with Di isopropyl ether and dried to get Form I, m.p.=184-186° C., $[?]_D^{20}$=55.6, Yield=85%.

EXAMPLE 4

Racemization of (R) Clopidogrel ($I_R$)

The mother liquor obtained from Example 2(a) was washed with the saturated sodium bicarbonate solution. The organic layer was separated and dried over anhydrous sodium sulfate. The organic layer was concentrated under vacuum to obtain the oily liquid. The 10 g (0.031 mole) of oily liquid was then dissolved in 50 mL Di isopropyl ether and to this 2 g (0.017 mole) of potassium-tert-butoxide was added at room temperature. After 12 Hrs, potassium tert-butoxide was neutralized with acetic acid. The organic phase was extracted with 50 mL water thrice. The organic phase was dried over anhydrous sodium sulfate and concentrated to obtain the oily liquid, yield 75%. The racemic clopidogrel thus obtained was resolved with the process described in example 3.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

We claim:

1. A process of preparation of (S)-(+)-α-(o-chlorophenyl)-6,7-dihydrothieno [3,2-c] pyridine-5 (4H)-acetate bisulfate, which comprises;
   a) condensing 4,5,6,7-Tetrahydrothieno [3,2-c] pyridine hydrochloride with α-bromo-2-chloroquine acetic acid methyl ester in an organic solvent at an ambient temperature in presence of an inorganic base to obtain racemic Clopidogrel base;
   b) resolving the racemic clopidogrel base using levo rotatory camphor-10- sulphonic acid in a mixture of organic solvents under stirring for 6-12 hrs within a temperature of range of 0-70° C;
   c) purifying the obtained (S)-Clopidogrel camphor sulfonate salt in a ketonic solvent;
   d) converting the (S)-Clopidogrel camphor sulfonate salt to (S)-Clopidogrel free base by separating the camphor sulfonic acid moiety from the (S)- Clopidogrel camphor sulfonate salt;
   e) dissolving (S)-Clopidogrel free base in a solubilizing solvent to form a clear solution;
   f) adding the solution of sulfuric acid in anti-solvent within temperature range 0-25° and stirring the obtained solution for several hours;
   g) filtering the separated solid to get crystalline (S)-Clopidogrel bisulfate having two crystallographically independent cations of clopidogrel and two independent bisulfate anions, wherein said two independent cations are of similar conformation.

2. The process as claimed in claim 1 wherein said organic solvent is dipolar aprotic solvent.

3. The process as claimed in claim 1 inorganic base is selected from sodium bicarbonate and potassium bicarbonate.

4. The process as claimed in claim 1 wherein said racemic clopidogrel base is extracted with lower halogenated hydrocarbon.

5. The process as claimed in claim 1 wherein the said resolution is carried out at temperature 25-55° C.

6. The process as claimed in claim 1 wherein said ketonic solvent is selected from acetone, 2-butanone, 3-pentanone, methyl iso-butyl ketone.

7. The process as claimed in claim 1 wherein said mixture of organic solvents are selected from alphatic ketones and aliphatic ethers.

8. The process as claimed in claim 1 wherein said mixture of solvents are used in a proportion ranging from 1:9 to 1:1.

9. The process as claimed in claim 1 wherein said proportion of mixed organic solvent is 1:1 .

10. The process as claimed in claim 7 wherein said ketone is selected from the group comprising of acetone, 2-butanone, 3-pentanone, methyl iso-butyl ketone.

11. The process as claimed in claim 7 wherein said ether is selected from the group comprising of di ethyl ether, di isopropyl ether, methyl-tert-butyl ether.

12. The process as claimed in claim 1 wherein said solubilizing solvent is $C_1$-$C_5$ carboxylic acid.

13. The process as claimed in claim 1, wherein said temperature range is about 0° C to 5° C.

14. The process as claimed in claim 1, wherein said anti-solvent is selected from the group of aliphatic ethers such as diethyl ether, di isopropyl ether, methyl-tert-butyl ether.

15. The process as claimed in claim 1, wherein said reaction mixture is stirred for 16 hours.

* * * * *

UNITED STATES PATENT AND TRADEMARK OFFICE
CERTIFICATE OF CORRECTION

| | | |
|---|---|---|
| PATENT NO. | : 7,446,200 B2 | Page 1 of 1 |
| APPLICATION NO. | : 11/149646 | |
| DATED | : November 4, 2008 | |
| INVENTOR(S) | : Manoj M. Deshpande et al. | |

It is certified that error appears in the above-identified patent and that said Letters Patent is hereby corrected as shown below:

Column 10, line 6, replace the word "chloroquine" with the word --chlorophenyl--

Signed and Sealed this

Nineteenth Day of May, 2009

JOHN DOLL
*Acting Director of the United States Patent and Trademark Office*